United States Patent
Crimmins

[11] Patent Number: 5,973,161
[45] Date of Patent: Oct. 26, 1999

[54] ENANTIOSELECTIVE SYNTHESIS OF CYCLOPENTENES

[75] Inventor: Michael T. Crimmins, Durham, N.C.

[73] Assignee: The University of North Carolina at Chapel Hill, Chapel Hill, N.C.

[21] Appl. No.: 08/818,357

[22] Filed: Mar. 17, 1997

Related U.S. Application Data

[60] Provisional application No. 60/013,626, Mar. 18, 1996, and provisional application No. 60/017,510, May 10, 1996.

[51] Int. Cl.$^6$ .................. C07D 277/14; C07D 263/20; C07D 275/06
[52] U.S. Cl. .................. 548/188; 548/208; 548/230
[58] Field of Search .................. 548/188, 208, 548/230

[56] References Cited

PUBLICATIONS

Hammer, Terahedron, 53(16) 5925, 1997.

*Primary Examiner*—Robert Gerstl
*Attorney, Agent, or Firm*—Myers Bigel Sibley & Sajovec

[57] ABSTRACT

Methods of synthesizing compounds of the Formula V:

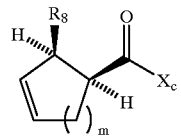

(V)

wherein $X_c$ is a chiral auxiliary, m is from 1 to 4, and $R_8$ is hydrogen or —OH, are provided.

Additionally, methods of synthesizing compounds of the Formula XII:

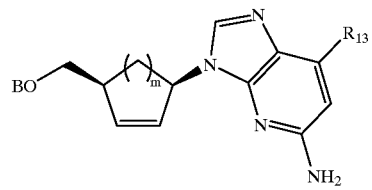

(XII)

wherein m is from 1–4;
B is hydrogen or a blocking group; and $R_{13}$ is a leaving group or a compound of formula $R_{14}$—N—$R_{15}$;
wherein $R_{14}$ is hydrogen or branched or straight-chain C1–C6 alkyl; and $R_{15}$ is hydrogen, C3–C8 cycloalkyl, or branched or straight-chain alkyl;
are also provided. Novel compounds useful in the synthesis of cyclopentenes and carbocyclic nucleosides are further provided.

18 Claims, No Drawings

ENANTIOSELECTIVE SYNTHESIS OF CYCLOPENTENES

RELATED APPLICATIONS

This application claims the benefit of U.S. Provisional Application No. 60/013,626 filed Mar. 18, 1996, and U.S. Provisional Application No. 60/017,510 filed May 10, 1996.

FIELD OF THE INVENTION

The present invention relates to methods and intermediates useful for the synthesis of cyclopentenes and carbocyclic nucleosides.

BACKGROUND OF THE INVENTION

U.S. Pat. No. 5,034,394 to Daluge discusses 6-substituted purine carbocyclic nucleosides of the general formula

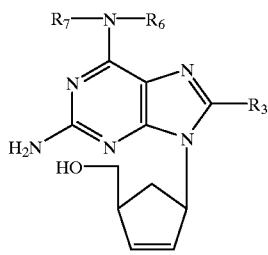

(I)

wherein $R_3$ represents hydrogen or $C_{1-6}$ alkyl; $R_6$ represents $C_{3-8}$ cycloalkyl, and $R_7$ represents a hydrogen atom or branched or straight chain $C_{1-6}$ alkyl; or a pharmaceutically acceptable ester or pharmaceutically acceptable salt thereof. Particularly preferred compounds of the Daluge '394 invention include (−)-cis-4-[2-amino-6-(cyclopropylamino-9H-purin-9-yl]-2-cyclopentene-1-methanol and (−)-cis-4-[2-amino-6-(cyclopropylmethylamino-9H-purin-9-yl]-2-cyclopentene-1-methanol or racemic or partially resolved enantiomers thereof.

European Patent Application No. EP 0 434 450 A2 to Daluge discusses enantiomeric compounds of the general formula

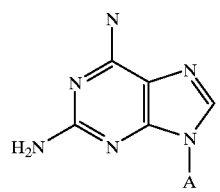

(II)

wherein R represents a cyclopropylamino or N-cyclopropyl-N-methylamino group, and A represents the 2-cyclopentene-1-methanol-4-yl group in either the (1S,4R) or (1R,4S) configuration and their derivatives, with compounds and their derivatives each being in the form of an enantiomer substantially free of the corresponding enantiomer.

PCT Application No. WO 92/18444 to Evans et al. discloses enantiomers of cyclopentene given as the following formulae:

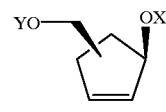

(IIIa)

(IIIb)

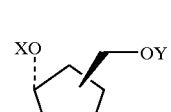

(IVa)

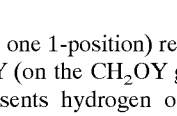

(IVb)

wherein X (at the one 1-position) represents hydrogen or an acyl group, and Y (on the $CH_2OY$ group at either the 4- or 5-position) represents hydrogen or a group that can be readily replaced by hydrogen, optionally substituted by non-interfering substituents. The compounds may be made by biocatalyst-mediated esterification of the racemic secondary alcohols, or deesterification of acyl derivatives or the racemic alcohols. These compounds are useful in the preparation of optionally-protected carbocyclic nucleosides, wherein a heterocyclic base is reacted with an enantiomer IIIa or IIIb by displacement of an acycloxy group. Alternatively, the protected carbocyclic nucleosides may be prepared by reacting a heterocyclic base with enantiomer IVa or IVb, wherein OX is a strong leaving group, via direct $S_N2$ displacement.

DETAILED DESCRIPTION OF THE INVENTION

As used herein, the term "alkyl" refers to C1 to C10 linear or branched alkyl, such as methyl, ethyl, propyl, butyl, isopropyl, sec-butyl, and tert-butyl. Methyl is currently preferred. The term "aryl" as used herein refers to C6 to C10 cyclic aromatic groups such as phenyl, naphthyl, and the like, and includes substituted aryl groups such as tolyl.

As noted above, the present invention provides a method of producing a compound of Formula V:

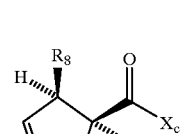

(V)

wherein $X_c$ is a chiral auxiliary;
$R_8$ is hydrogen or —OH; and
and m is from 1 to 4, preferably from 1 to 2, and most preferably 1.

In a preferred embodiment of the invention, the chiral auxiliary $X_c$ is selected from the group consisting of (A)

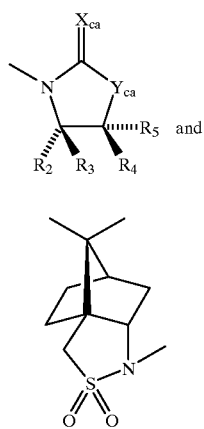

wherein $X_{ca}$ is S or O;
$Y_{ca}$ is S or O;
$R_2$ is hydrogen, alkyl, aryl or alkylaryl;
$R_3$ is hydrogen, alkyl, aryl or alkylaryl;
$R_4$ is hydrogen, alkyl, aryl or alkylaryl; and
$R_5$ is hydrogen, alkyl, aryl or alkylaryl.

Referring now to SCHEME 1, the synthesis of compound of Formula V is represented by the ring-closing metathesis reaction shown in Step 3.

In Step 3, a compound of Formula VI

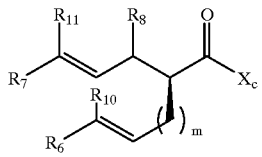

(VI)

wherein $X_c$ and $R_8$ are defined as provided above;
$R_6$ is hydrogen, alkyl or aryl;
$R_7$ is hydrogen, alkyl or aryl;
$R_{10}$ is hydrogen, alkyl or aryl; and
$R_{11}$ is hydrogen, alkyl or aryl;
is reacted with a metathesis catalyst to produce the compound of Formula V. Any catalyst that facilitates the desired reaction is embraced by the scope of this invention, although metal catalysts such as ruthenium carbene complexes and pentacoordinate ruthenium alkylidene complexes are preferred. Ruthenium carbene complex catalysts are discussed in G. C. Fu et al., *J. Am. Chem. Soc*. 115, 9856-9857 (1993); ruthenium alkylidene catalyst complexes of the general form

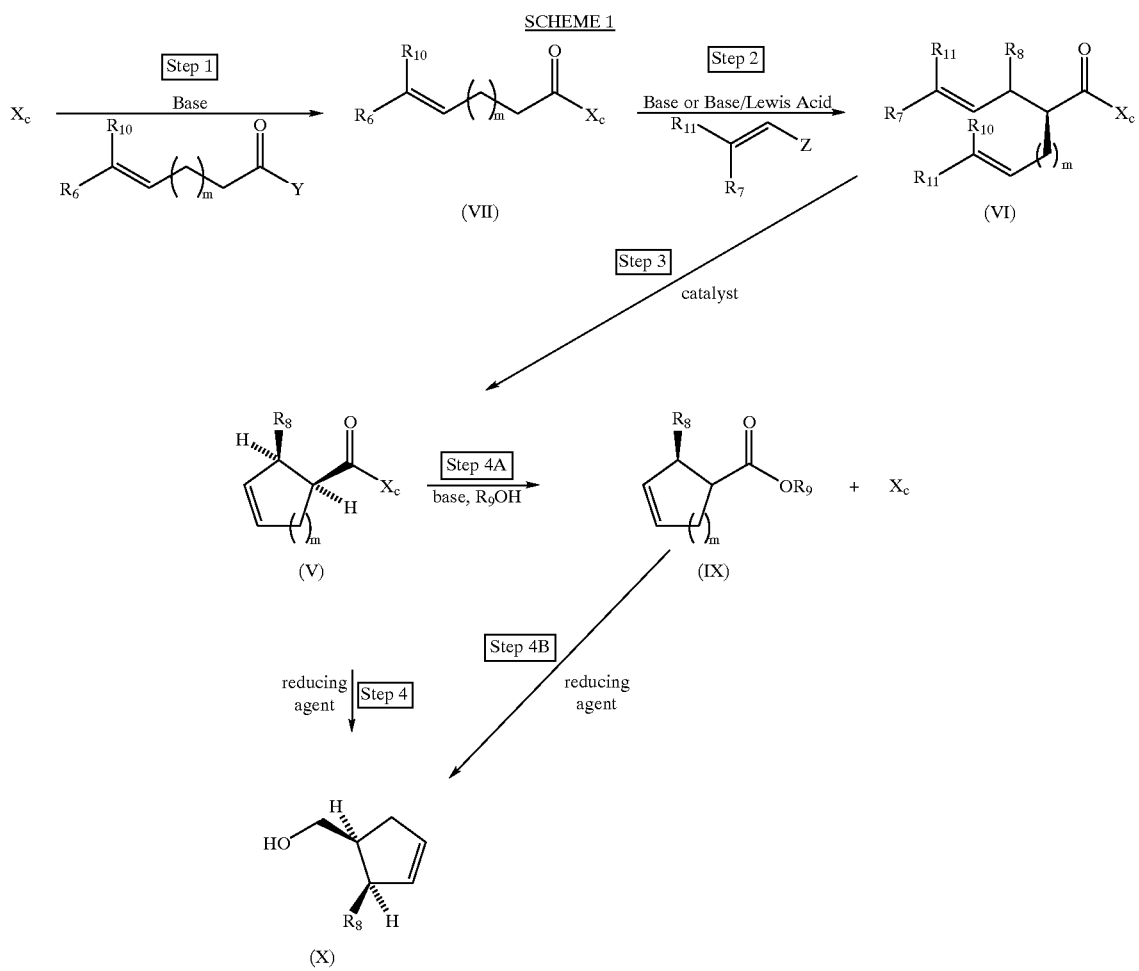

SCHEME 1

RuCl$_2$(=CHR) (PR'$_3$)$_2$ are discussed in P. Schwab et al., *J. Am. Chem. Soc* . 118, 100–110 (1996) (applicants specifically intend the disclosures of these references be incorporated herein in their entirety).

Ruthenium and osmium metal complexes are also useful as catalysts in the present invention. Several of these catalysts are disclosed in U.S. Pat. Nos. 5,342,909 and 5,312,940, both to Grubbs et al. (applicants specifically intend the disclosures of these patent references be incorporated herein in their entirety). In particular, catalysts of the formula:

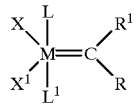

wherein:

M is Os or Ru;

R and R$^1$ are independently selected from hydrogen, C2–C20 alkenyl, C2–C20 alkynyl, C1–C20 alkyl, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl or C1–C20 alkylsulfinyl; each optionally substituted with C1–C5 alkyl, halogen, C1–C5 alkoxy or with a phenyl group optionally substituted with a halogen, C1–C5 alkyl, or C1–C5 alkoxy;

X and X$^1$ are independently selected from any ionic ligand; and

L and L$^1$ and are independently selected from any neutral electron donor;

are of particular use in this invention. As provided hereinabove, 2,3, or 4 of the moieties X, X$^1$, L, and L$^1$ can be taken together to form a chelating multidentate ligand.

The reaction of Step 3 is carried out in a polar or nonpolar, inert, protic or aprotic, organic solvent. Suitable solvents include straight-chained hydrocarbons (e.g., n-heptane, n-hexane); branched-chain hydrocarbons (e.g., isobutane, isopentane, 2-methylpentane); alicyclics (e.g., cyclopentane, cyclohexane); alcohols (e.g., methanol, butanol, cyclohexanol); halogenated hydrocarbons (e.g., dichloromethane, methylene dichloride, chloroform, carbon tetrachloride, dichloroethane, trichloroethane); aromatic hydrocarbons (e.g., benzene, toluene, xylene, cumene, cymene, mesitylene, diisopropylbenzene); aliphatic ethers (e.g., diethyl ether, diisopropyl ether, di-n-butyl ether), and alicyclic ether (e.g. tetrahydrofuran, tetrahydropyran).

The reaction temperature of Step 3 is not critical, and is typically from about –78° C. or –20° C. to about 150° C. The catalyst is included in an effective catalytic amount, from about 0.001 Mole percent to 100 Mole percent (stoichiometric), and typically about 1.0 or 2.0 Mole percent. The reaction atmosphere is not critical, but the reaction is preferably carried out to the exclusion of oxygen by running the reaction in a nitrogen atmosphere, or by purging the reaction vessel with nitrogen or argon prior to carrying out the reaction. The reaction may be carried out with stirring. The duration of the reaction is not critical, but may be about one hour.

The compound of Formula VI used in the synthesis of the compound of Formula V may be produced by the reaction represented in SCHEME 1 by Step 2. In Step 2, a compound of Formula VII:

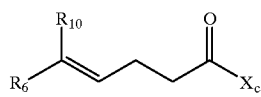

with m, X$_c$, R$_6$, and R$_{10}$ defined as provided above, is reacted with an electrophilic compound of the formula:

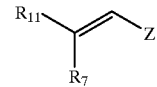

with Z being selected from the group consisting of aldehydes and alkyl halides, and R$_7$ and R$_{11}$ defined as provided above. In one embodiment of the invention, the electrophilic compound is acrolein.

The reaction of Step 2 is carried out either with a base (e.g., lithiumdiisopropyl amide), or with a mixture of a base and a Lewis acid (e.g., a tertiary amine along with a dialkyl boron triflate). In one embodiment of the invention, Step 2 is carried out in a base/Lewis acid combination of dibutyl-boron triflate and triethyl amine.

The reaction of Step 2 is carried out in an inert, aprotic, polar or nonpolar organic solvent as provided above in Step 3. The reaction temperature of Step 2 is not critical, and is typically from about –78°0 C. to about 25° C. The reaction atmosphere is not critical, but the reaction is preferably carried out in a nitrogen atmosphere, to the exclusion of water. The reaction may be carried out with stirring. The duration of the reaction is not critical, but may be about one hour.

In an alternative embodiment of the invention, the compound of Formula VI may be produced by the following reaction:

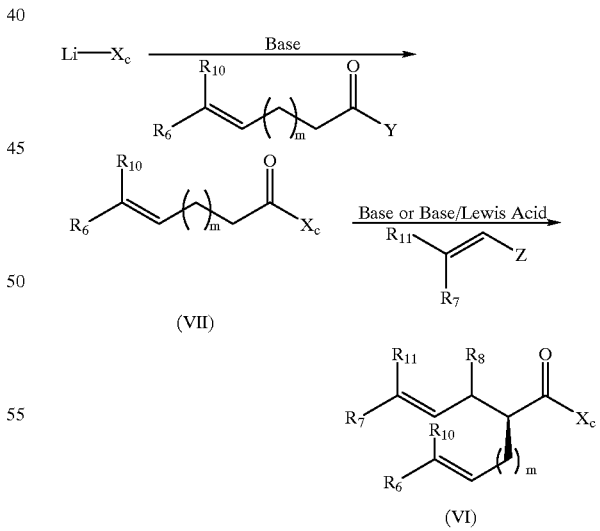

wherein X$_c$, m, Y, Z, R$_6$, R$_7$, R$_8$, R$_9$, R$_{10}$, and R$_{11}$ are as given above. This reaction may be carried out under the reaction conditions provided above for Step 2.

In another alternative embodiment of the invention, the compound of Formula VI may be produced by the following reaction:

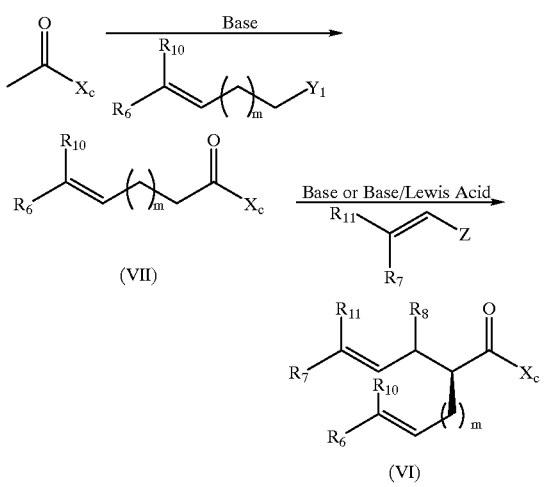

(VII)

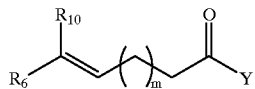

(VI)

wherein $X_c$, m, Z, $R_6$, $R_7$, $R_8$, $R_9$, $R_{10}$, and $R_{11}$ are as given above, and $Y_1$ is a halogen group, with bromo-groups and iodo-groups preferred. This reaction may also be carried out under the reaction conditions provided above for Step 2.

Another aspect of the present invention is a method of synthesizing the compound of Formula VII, above. This synthesis is illustrated in SCHEME 1 as Step 1. In Step 1, chiral auxiliary $X_c$ as provided above is contacted with a base and a compound of the formula

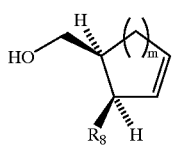

wherein m, $R_6$, and $R_{10}$ are as provided above, and Y is a strong leaving group selected from the group consisting of halogens and carboxylates. In one preferred embodiment of the invention, the leaving group Y is pivalate.

The reaction of Step 1 is carried out in an inert, aprotic, polar or nonpolar organic solvent as provided in Step 2 and Step 3, above. Any base is suitable, although a base selected from the group consisting of n-butyllithium or sodium hydride is preferred. The base may be provided in stoichiometric quantities or lesser amounts. The reaction temperature is not critical, and is typically from −78° C. to 100° C. The reaction is preferably carried out in a nitrogen atmosphere in the absence of water.

Additional aspects of this invention include methods that utilize the compound of Formula V as given above to produce intermediates useful in other synthesis reactions, including the synthesis of carbocyclic nucleosides. Accordingly, one aspect of the invention is the production of a compound of Formula X

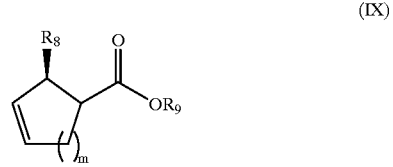
(X)

wherein $R_8$ is hydrogen or —OH. This synthesis, represented as Step 4 in SCHEME 1, comprises the contacting of a compound of Formula V with a reducing agent to produce the compound of Formula X. Any suitable reducing agent may be used, although lithium-containing reducing agents such as $LiBH_4$ or $LiAlH_4$ are preferred. The reaction of Step 4 is carried out in an inert, protic or aprotic, polar or nonpolar organic solvent as provided in Steps 1–3, above.

In an alternative embodiment of the present invention, a compound of Formula V is reacted with a base and a compound of the formula $R_9OH$ to regenerate the chiral auxiliary $X_c$ as provided above, and a compound of Formula IX:

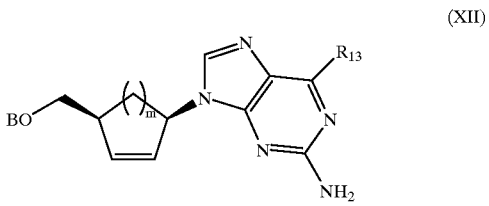
(IX)

wherein $R_8$ and m are as provided above, and $R_9$ is hydrogen, alkyl, aryl, or alkylaryl. This transesterification reaction is illustrated as Step 4A in SCHEME 1. After Step 4A is completed, the alkyl ester or aryl ester produced may then undergo the reactions shown in Step 4 to produce the compound of Formula X.

The present invention also provides a method of producing a compound of Formula XII:

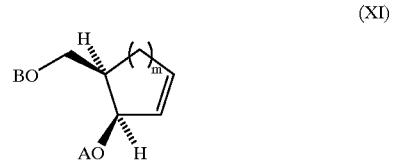
(XII)

wherein m is as defined above;
B is a hydrogen or a blocking group; and
$R_{13}$ is a leaving group or a compound of formula $R_{14}$—N—$R_{15}$, wherein
   $R_{14}$ is hydrogen or branched or straight-chain C1–C6
   $R_{15}$ is hydrogen, C3–C8 cycloalkyl or branched or straight-chain C1–C6 alkyl.

Referring now to SCHEME 2, the synthesis of the compound of Formula XII is represented by the catalyzed displacement reaction shown in Step 6. In Step 6, a compound of formula XI

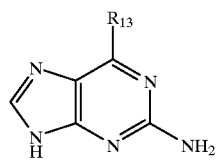
(XI)

wherein m and B are as defined above; and
A is an activating group; is reacted with a catalyst and a group of the formula

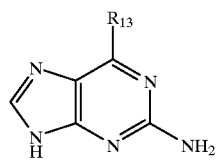

wherein $R_{13}$ is a leaving group or a compound of formula $R_{14}$—N—$R_{15}$, wherein $R_{14}$ is hydrogen or branched or straight-chain C1–C6 alkyl; and $R_{15}$ is hydrogen, C3–C8 cycloalkyl or branched or straight-chain C1–C6 alkyl, to produce the compound of Formula XII.

The blocking group as provided herein may be any such group recognized in the art of organic chemistry as suitable for protecting hydroxymethyl groups under the conditions of Step 6. Examples of suitable blocking groups include those reported in T. W. Green, *Protecting Groups in Organic Synthesis* (chapter 2, 1981). Typically, the blocking group will be a

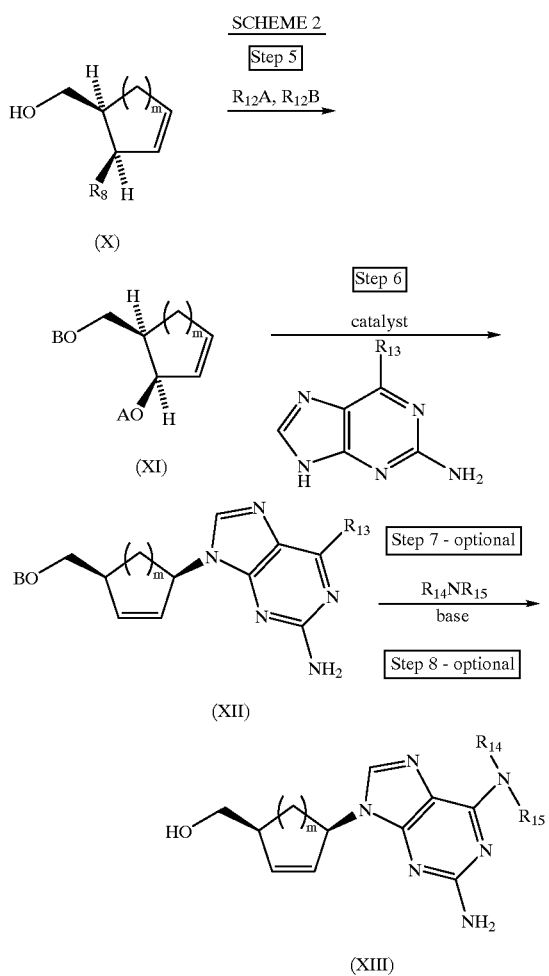

sterically hindered ether (e.g., trialkylsilyl ether, triphenylmethyl ether), a carboxylate, a C1–C20 alkylester, or a C1 to C20 ester of a carbonic acid (e.g., methyl carbonate), or acetate. In one preferred embodiment of the invention, the blocking group is methyl carbonate or acetate.

The activating group as provided in Step 6 may be any group suitable for activating a secondary allylic hydroxy group for catalyzed displacement reactions. Examples of suitable secondary hydroxy-group activating groups include carbonates, carboxylates, C1–C20 alkanoic acid esters, aryloic acid esters, arylalkanoic acid esters, allyl ethers, aryloxy ethers and halo groups (e.g., chloro-, iodo-, bromo-). In one embodiment of the invention, the activating group is methyl carbonate or acetate.

In some cases, a single group can serve both the blocking and activating functions; that is, A and B may be identical (e.g., methyl carbonate, acetate).

$R_{13}$ is a leaving group or a compound of formula $R_{14}$—N—$R_{15}$, wherein $R_{14}$ is hydrogen or branched or straight-chain C1–C6 alkyl, with hydrogen preferred, and $R_{15}$ is hydrogen, C3–C8 cycloalkyl or branched or straight-chain C1–C6 alkyl, with cyclopropyl preferred. When $R_{13}$ is a leaving group, $R_{13}$ is a halo group, with chloro groups preferred.

Any catalyst that facilitates the desired reaction of Step 6 is embraced by the scope of the invention, although metal catalysts are preferred. In a particular embodiment of the invention, Pd(O) complexes, for example tetrakis (triphenylphosphine)-palladium(O), are used as the catalyst in Step 6.

The reaction of Step 6 is carried out in a polar or nonpolar, inert, aprotic organic solvent as described above, with polar solvents (e.g., THF, DMSO) being preferred. The reaction temperature of Step 6 is not critical, and is typically from about 0° to 100° C., and preferably from 25 ° to 45° C. The catalyst is included in an effective catalytic amount, from about 0.001 Mole percent to 100 Mole percent (stoichiometric), and typically about 2.0 to 5.0 Mole percent. The reaction atmosphere is not critical, but the reaction is preferably carried out to the exclusion of oxygen by running the reaction in a nitrogen atmosphere, or by purging the reaction vessel with nitrogen or argon prior to carrying out the reaction. The reaction may be carried out with stirring. The duration of the reaction is not critical, but may be about one hour.

The compound of Formula XI used in the synthesis of the compound of Formula XII may be produced by the reaction represented in SCHEME 2 by the displacement reaction of Step 5. In Step 5, a compound of Formula X as provided above is reacted with the compounds of formulae $R_{12}A$ and $R_{12}B$, with each $R_{12}$ being independently selected from the group consisting of halo groups and carboxylates, and A and B are as defined above. The reaction of Step 5 is carried out in a polar or nonpolar, inert, aprotic organic solvent as described above. Other reaction conditions, including temperature and atmosphere, will be apparent to one skilled in the art.

In one alternative embodiment of the invention, when $R_{13}$ of the compound of Formula XII is a leaving group, the compound of Formula XII may be further reacted with a base and a compound of the Formula $R_{14}$—N—$R_{15}$, with $R_{14}$ and $R_{15}$ as defined above, to produce a compound of the formula XIII:

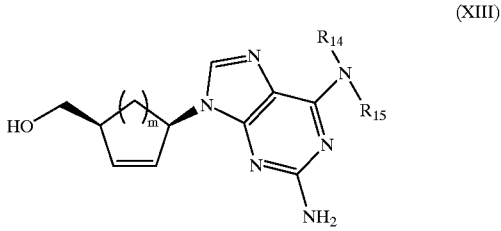

(XIII)

This synthesis, represented as optional Steps 7 and 8 in SCHEME 2, comprises the contacting of a compound of Formula XII, when $R_{13}$ is a leaving group, with a compound of the formula $R_{14}$—N—$R_{15}$ (Step 7), followed by reacting the compound with a base (Step 8).

The reactions of Step 7 and Step 8 are carried out in an inert, protic or aprotic, polar or non-polar organic solvent as provided above. Any suitable base may be used, although sodium hydroxide is preferred. The base may be provided in stoichiometric or lesser amounts. The reaction temperature is not critical, and is typically from −78° to 100° C. Other suitable reaction conditions will be apparent to one skilled in the art.

Within the scope of the present invention, compounds of Formulae XII and XIII, in addition to being produced by the methods illustrated in SCHEME 2, may also be produced by the alternative methods in which blocking and activating groups are not used, and wherein the chiral auxiliary $X_c$ is removed after the ring-closing metathesis reaction described above as Step 3 of SCHEME 1. Turning now to SCHEME 3, a compound of Formula V is produced as in Step 3, described above. In Step 3.1, the compound of formula V is reacted with a catalyst and a compound of the formula preferred. In a particular embodiment of the invention, Pd(O) complexes, for example tetrakis(triphenylphosphine)-palladium(O), are used as the catalyst in Step 3.1. Alternatively, the compound of Formula XII is produced by the reaction steps illustrated in SCHEME 3 as Steps 3.1A, 3.2 and 3.3. In Step 3.1A, the compound of Formula V is reacted with a catalyst and a compound of the formula

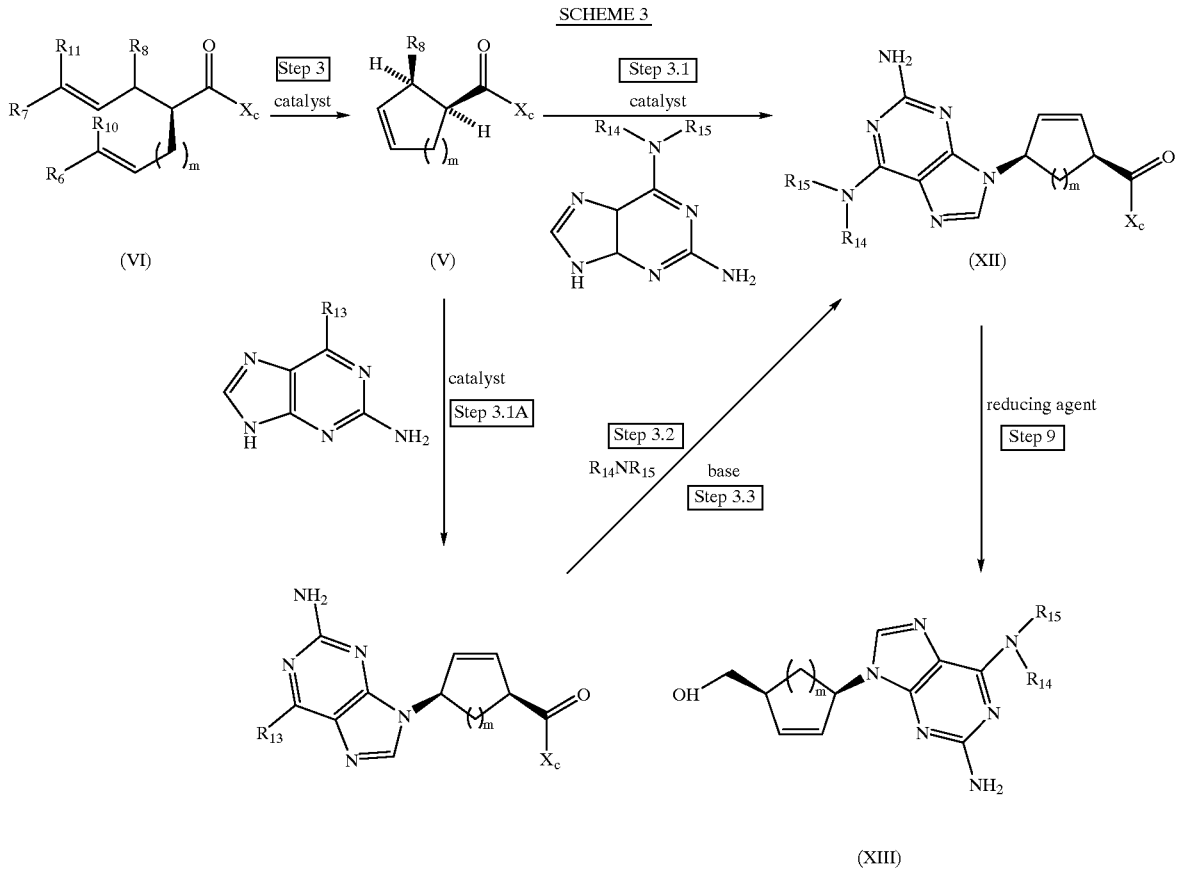

(VI) (V) (XII) (XIII)

SCHEME 3

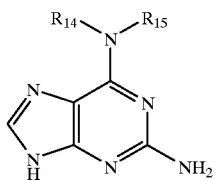

wherein $R_{14}$ and $R_{15}$ are as defined above, to produce a compound of Formula XII as defined above. Any catalyst that facilitates the desired reaction of Step 3.1 is embraced by the scope of the invention, although metal catalysts are wherein $R_{13}$ is a halogen group, and is preferably a chloro-group. Any catalyst that could be used in Step 3.1, above, may also be used in Step 3.1A. The resulting compound is then reacted with a compound of formula $R_{14}$—N—$R_{15}$ (Step 3.2) and a base (Step 3.3) to produce the compound of Formula XII. The conditions of Steps 3.2 and 3.3 will be essentially the same as those described for Steps 7 and 8 of SCHEME 2, above. If desired, the compound of Formula XII may further be reacted with a reducing agent (Step 9) to produce a compound of Formula XIII, as defined above. Suitable reducing agents and reaction conditions for Step 9 will be essentially the same as those suitable for carrying out Step 4 of SCHEME 1, above.

As illustrated in both SCHEME 2 and SCHEME 3, compounds of Formulae XII and XIII may be produced using methods in which the chiral auxiliary is removed from the reactive compound after the ring-closing metathesis step of Step 3. However, the present invention also provides methods of producing the compounds of Formulae XII and XIII whereby the chiral auxiliary is removed prior to the ring-closing metathesis step. Preferred embodiments of these methods are schematically illustrated in SCHEME 4:

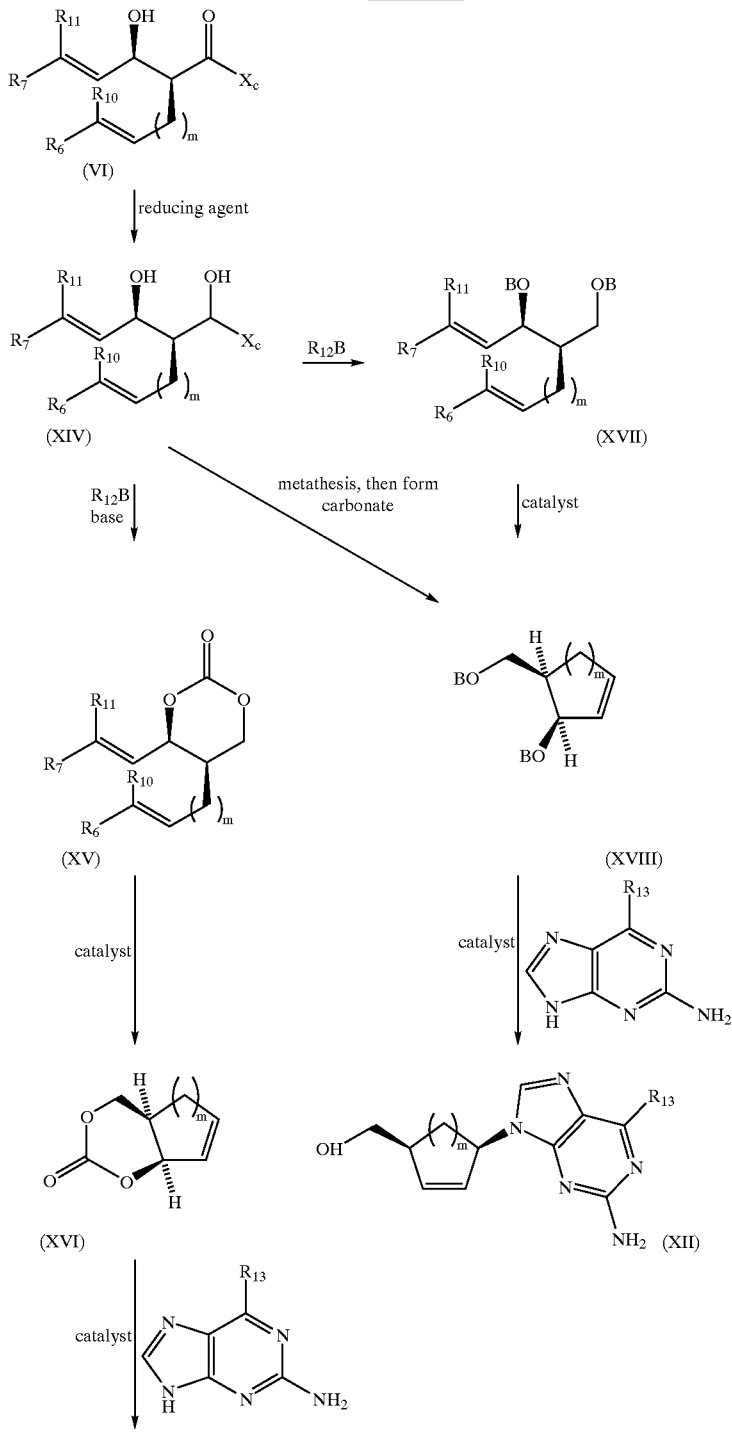

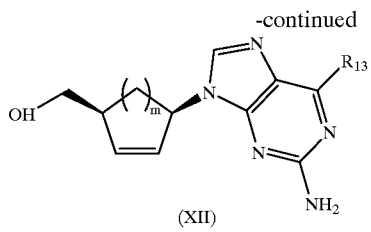

(XII)

As indicated in SCHEME 4, one method of the invention in which the chiral auxiliary is removed prior to the ring-closing metathesis step begins with a compound of Formula VI, as provided above. This compound is reacted with a reducing agent to provide a compound of Formula XIV:

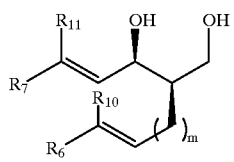

(XIV)

Any suitable reducing agent may be used, although lithium-containing reducing agents such as $LiBH_4$ or $LiAlH_4$ are preferred. This reaction 4 is carried out in an inert, protic or aprotic, polar or nonpolar organic solvent as provided above. This compound of Formula XIV is then reacted with a compound of $R_{12}B$, as defined above, and a base, to produce a compound of Formula XV:

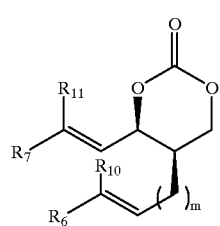

(XV)

This compound of Formula XV is then reacted with a catalyst and under conditions provided as in the ring-closing metathesis step Step 3 of SCHEME 1 above, to produce a compound of Formula XVI:

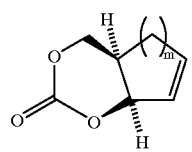

(XVI)

This compound of Formula XVI is then reacted under the conditions of Step 6 in SCHEME 2 to produce the compound of Formula XII, and may further reacted under the conditions of Step 7 and Step 8 to produce a compound of Formula XIII.

Alternatively, when removal of the chiral auxiliary prior to the ring-closing metathesis step is desired, the compound of Formula XIV is reacted with a compound of formula $R_{12}B$ to produce a compound of Formula XVII:

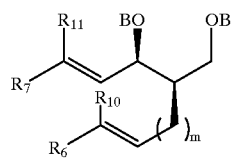

(XVII)

This compound of Formula XVII may then be subject to the ring-closing metathesis conditions of Step 3 above, to produce a compound of Formula XVIII:

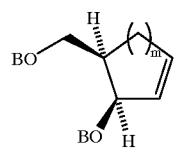

(XVIII)

This compound of Formula XVIII is then reacted under the conditions of Step 6 in SCHEME 2 to produce the compound of Formula XII, and may further reacted under the conditions of Step 7 and Step 8 to produce a compound of Formula XIII.

The methods of the present invention and the novel compounds disclosed herein are useful in the synthesis of carbocyclic nucleosides and cyclopentene compounds, which are useful in the treatment of infections caused by Human Immunodeficiency Virus (HIV) and Hepatitis B Virus (HBV). Carbocyclic nucleosides effective in the treatment of HIV and HBV are disclosed in U.S. Pat. No. 5,034,394 to Daluge, the disclosure of which is incorporated herein in its entirety.

The present invention is explained in greater detail in the following non-limiting Examples, in which g means grams, mg means milligrams, mmol means millimolar, mL means milliliter, h means hour(s), THF means tetrahydrofuran, tlc means thin-layer chromatography, min means minutes, NMR means nuclear magnetic resonance, Hz means hertz, cm means centimeter, IR means infrared, $[\alpha]_D^{24}$ denotes specific rotation at 24° C., c denotes density of the pure liquid in g/100 mL, δ means chemical downshift from trimethylsilane (TMS) in parts per million (ppm), J denotes coupling constant, and temperatures are given in degrees Centigrade.

EXAMPLE 1

[4S]-3-(1-oxo-4-pentenyl)-4-benzyl-2-oxazolidinone
(Formula VII Compound)

To a cooled solution (−78° C.) of 4-pentenoic acid (10.0 g, 100 mmol) and 14.7 mL (105 mmol) of triethyl amine in 800 mL of diethyl ether was added 12.35 mL (100 mmol) of pivaloyl chloride. After 5 min the bath was removed and replaced by an ice water bath. The heterogeneous mixture was mechanically stirred at 0° C. for 1 h.

In a separate flask, a solution of 17.7 g (100 mmol) of (S)-4-benzyl-2-oxazolidinone in 120 mL of THF was cooled to −78° C. whereupon 63.1 mL (101 mmol) of 1.6 M n-butyllithium in hexanes was added slowly. This solution was stirred for 10 min at −78° C. The flask containing the mixed anhydride was cooled to −78° C. and the lithiated oxazolidinone was cannulated into the mixed anhydride. After stirring at −78° C. for 15 min, the reaction mixture was warmed to 0° C. and stirred for 30 min. After quenching with water, the layers were separated and the aqueous layer was washed with ether. The combined organic layers were washed with brine, dried, filtered and concentrated. The residue was purified by filtration through a pad of silica gel (3:1 hexanes: ethyl acetate) to give 25.88 g (100%) of the title compound as a colorless oil. $^1$H NMR (CDCl$_3$) δ 2.42 (m,2H); 2.72 (dd, J=9.7, 13 Hz, 1H); 3.03 (m, 2H; 3.29 (dd, J=13, 4 Hz, 1H); 4.15 (m, 2H); 4.65 (m,1H); 5.07 (m,2H); 5.86 (m, 1H); 7.12–7.37 (m, 5H). $^{13}$C NMR (CDCl$_3$) δ 28.17, 34.78, 37.9, 55.14, 66.2, 115.7, 127.3, 128.9, 129.4, 135.2, 136.7, 153.4, 172.5. IR (film) 1790, 1708, 1390 cm$^{-1}$ [α]$^{24}$D+64.22° (c=0.83, CHCl$_3$) Anal: Calcd. for C$_{15}$H$_{17}$O$_3$N: C, 69.48; H, 6.61; N, 5.40. Found: C, 69.20; H, 6.65; N, 5.33.

EXAMPLE 2

[3(2S,3R),4S]-3-(3-Hydroxy-2-allyl-1-oxo-4-pentenyl)-4-benzyl-2-oxazolidinone (Formula VI Compound)

A solution of the [4S]-3-(1-oxo-4-pentenyl)-4-benzyl-2-oxazolidinone (2.59 g, 10 mmol) in 20 mL of dichloromethane was cooled to −15° C. Dibutylboron triflate (2.75 mL, 11 mmol) was added dropwise followed by dropwise addition of triethylamine (1.67 mL, 11 mmol). This addition is exothermic. The solution was stirred at 0° C. for 15 min and then cooled to −78° C. The freshly distilled acrolein (0.75 mL, 11 mmol) was then added neat and the mixture was stirred for 1.5 h at −78° C. and warmed to 0° C. for 30 min. Then 12 mL of pH 7.1 buffer was added followed by 40 mL of methanol and dropwise addition of 12 mL of 30% hydrogen peroxide (0° C. bath). After stirring for 1 h, the mixture was concentrated and extracted with ethyl acetate. The organic layer was washed with 10% sodium bisulfite and brine and then dried, filtered and concentrated. Filtration through a silica gel column (3:1 hexanes: ethyl acetate) of the residue afforded 2.41 g (77%) of a viscous, colorless oil. $^1$H NMR (CDCl$_3$) δ 2.38–2.61 (band, 3H); 2.62 (dd, J=10.5, 13 Hz, 1H); 3.28 (dd, J=13, 4 Hz, 1H); 4.13 (m, 2H); 4.22 (m, 1H); 4.42, (m, 1H); 4.69 (m, 1H); 4.98–5.37 (m, 4H); 5.72–5.96 (m, 2H); 7.12–7.34 (m, 5H). $^{13}$C NMR (CDCl$_3$) δ 31.89, 37.87, 47.23, 55.4, 65.88, 73.13, 116.6, 117.1, 127.2, 128.8, 129.3, 135.1, 135.2, 137.2, 153.4, 174.3. IR (film) 3500, 1780, 1695, 1385 cm$^{-1}$ . [α]$^{24}$D+50.56° (c=0.89, CHCl$_3$). Anal: Calcd. for C$_{18}$H$_{21}$O$_4$N: C, 68.55; H, 6.71: N, 4.44. Found: C, 68.65; H, 6.74; N, 4.40.

EXAMPLE 3

[3(2S,3R),4S]-3-(3-Hydroxy-2-allyl-1-oxo-4-pentenyl)-4-benzyl-1,3-oxazolidine-2-thione (Formula VI Compound)

A solution of [4S]-3-(1-oxo-4-pentenyl)-4-benzyl-1,3-oxazolidine-2-thione (0.233 g, 0.84 mmol) in 5 ml of dichloromethane was cooled to 0° C. Titanium tetrachloride (0.10 ml, 0.93 mmol) was added dropwise, followed by dropwise addition of (−)-sparteine (0.49 ml, 2.1 mmol). The solution was stirred at 0° C. for 20 min and then cooled to −78° C. Freshly distilled acrolein (0.09 ml, 1.3 mmol) was then added neat, and the mixture stirred for 1 h at −78° C. and warmed to 0° C. for 30 min. Then 6 ml of a half-saturated ammonium chloride solution was added and the mixture warmed to room temperature. The resultant slurry was filtered through celite and the layers were separated. The water layer was back-extracted three times with dichloromethane. The combined organic layers were dried, filtered, and concentrated. Purification by silica gel chromatography (4:1 hexanes:ethyl acetate) of the residue afforded 0.255 g (91%) of a viscous, colorless oil. $^1$H NMR (CDCl$_3$) δ 2.39–2.75 (m, 4H); 3.23 (dd, J=4.8. 13.8 Hz, 1H); 4.18–4.32 (m, 2H); 4.50 (m, 1H); 4.88–5.41 (m, 6H); 5.79–6.03 (m, 2H); 7.12–7.38 (m, 5H). $^{13}$C NMR (CDCl$_3$) δ 31.66, 37.70, 46.88, 60.19, 70.10, 73.25, 116.7, 117.3, 127.4, 129.0, 129.3, 135.1, 137.4, 175.0, 185.6. IR (film) 3200–3690, 1690, 1640, 1495, 1470, 1360 cm$^{-1}$. [α]$^{24}$D+89.8° (c=1.2, CH$_2$Cl$_2$).

EXAMPLE 4

[3(1R,2R)4S]-4-benzyl-3-[(2-hydroxy-3-cyclopenten-1-yl)-carbonyl]-2-oxazolidinone (Formula V Compound)

To a solution of the [3(2S,3R),4S]-3-(3- Hydroxy-2-allyl-1-oxo-4-pentenyl)-4-benzyl-2-oxazolidinone (767 mg. 2.43 mmol) in 15 mL of dichloromethane under argon was added 40 mg of benzylidine(bis-tricyclohexylphosphine) ruthenium (II) dichloride. The dark mixture was stirred at 2520 C. for 30 min whereupon thin-layer chromatography showed complete reaction. Air was bubbled through the mixtured for 3 h to oxidize the remaining catalyst. Concentration followed by flash chromatography gave 679 mg (97%) of a light green oil. $^1$H NMR (CDCl$_3$) δ 2.00 (br, 1H), 2.48 (m, 1H); 2.76 (dd, J=10.5, 13 Hz, 1H); 3.12 (m, 1H); 3.31 (dd, J=13, 4 Hz, 1H); 4.15 (m, 2H); 4.45 (m, 1H), 4.69 (m, 1H); 5.09, (m, 1H); 5.74 (m, 1H); 6.02 (m, 1H); 7.15–7.36 (m, 5H). $^{13}$C NMR (CDCl$_3$) δ 33.19, 38.07, 47.03, 55.49, 66.2, 77.23, 127.2, 128.8, 129.3, 131.1, 134.7, 135.4, 153.6, 172.1. IR (film) 3480, 1780, 1700, 1380 cm$^{-1}$ [α]$^{24}$D −92.45° (c=0.795, CHCl$_3$). Anal: Calcd. for C$_{16}$H$_{17}$O$_4$N: C, 66.88; H, 5.96; N, 4.88. Found: C, 66.79; H, 5.92; N, 4.79.

EXAMPLE 5

(1R,5R)-5-hydroxymethyl-2-cyclopenten-1-ol (Formula X Compound)

A solution of [3(1R,2R)4S]-4-benzyl-3-[(2-hydroxy-3-cyclopenten-1-yl)-carbonyl]-2-oxazolidinone (339 mg, 1.18 mmol) in 11 mL of THF was cooled to 0° C. and 0.105 mL of methanol was added. Lithium borhydride solution (1.30 mL, 2.6 mmol) was added and gas evolution was observed. After stirring for 1 h at 0° C. the reaction was quenched by the addition of 3.5 mL of 10% sodium hydroxide solution. Diethyl ether (20 mL) was added and the layers were separated. The aqueous layer was extracted with ethyl acetate and the combined organic extracts was washed with brine, dried, filtered and concentrated. Flash chromatography of the residue provided 102 mg (76%) of the diol as a pale yellow oil. $^1$H NMR (CDCl$_3$) δ 2.03–2.49 (band, 3H), 3.33 (br s, 2H); 3.71 (m, 2H); 4.82 (m, 1H); 5.74 (m, 1H); 5.92 (m, 1H). $^{13}$C NMR (CDCl$_3$) δ 33.54, 42.49, 62.59, 77.61, 132.4, 135.0. IR (film) 3600–3000 (broad) cm$^{-1}$ [α]$^{24}$D−125.1° (c=0.47, CH$_2$Cl$_2$) (identical in all respects to an authentic sample). The diol was converted to its bis-p-toluate and analyzed by chiral HPLC on a chiralcel OD column eluting with 4% ethanol-heptane. Optical purity was determined to be ≧99% by this method. S,S enantiomer elution time=5.9 min; R,R enantiomer elution time=7.6 min.

The foregoing examples are illustrative of the present invention, and are not to be construed as limiting thereof.

The invention is defined by the following claims, with equivalents of the claims to be included therein.

That which is claimed is:

1. A method of producing a compound of formula V:

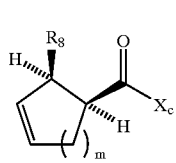

(V)

wherein $X_c$ is a chiral auxiliary selected from the group consisting of:

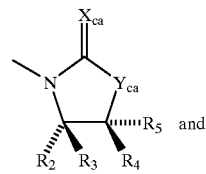

(A)

and

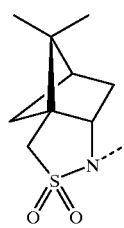

(B)

wherein $X_{ca}$ is S or O;
$Y_{ca}$ is S or O;
$R_2$ is hydrogen, alkyl, aryl or alkylaryl;
$R_3$ is hydrogen, alkyl, aryl or alkylaryl;
$R_4$ is hydrogen, alkyl, aryl or alkylaryl; and
$R_5$ is hydrogen, alkyl, aryl or alkylaryl;
$R_8$ is —OH; and
m is from 1 to 4;

comprising reacting in a organic solvent at a temperature between about −78° C. and about 150° C., a compound of Formula VI:

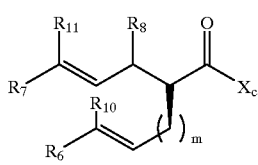

(VI)

wherein m, $X_c$ and $R_8$ are as provided in Formula V;
$R_6$ is hydrogen, alkyl or aryl;
$R_7$ is hydrogen, alkyl or aryl;
$R_{10}$ is hydrogen, alkyl or aryl, and
$R_{11}$ is hydrogen, alkyl or aryl;

with a catalyst of the formula:

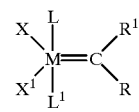

wherein;
M is Os or Ru;
R and $R^1$ are independently selected from hydrogen, C2–C20 alkenyl, C2–C20 alkynyl, C1–C20 alky, aryl, C1–C20 carboxylate, C1–C20 alkoxy, C2–C20 alkenyloxy, C2–C20 alkynyloxy, aryloxy, C2–C20 alkoxycarbonyl, C1–C20 alkylthio, C1–C20 alkylsulfonyl or C1–C20 alkylsulfinyl; each optionally substituted with C1–C5 alkyl, halogen, C1–C5 alkoxy or with a phenyl group optionally substituted with a halogen, C1–C5 alkyl, or C1–C5 alkoxy;
X and $X^1$ are each independently an ionic ligand; and
L and $L^1$ are each independently a neutral electron donor;

to produce the compound of Formula V.

2. A method according to claim 1, wherein the compound of Formula VI is [3(2S,3R),4S]-3-(3-Hydroxy-2-allyl-1-oxo-4-pentenyl)-4-benzyl-2-oxazolidinone.

3. A method according to claim 1, wherein the catalyst is benzylidine(bis-tricyclohexylphosphine) ruthenium (II) dichloride.

4. A method according to claim 1, wherein the compound of Formula V is [3(1R,2R)4S]-4-benzyl-3-[(2-hydroxy-3-cyclopenten-1-yl)-carbonyl]-2-oxazolidinone.

5. A method according to claim 1, whereby the compound of Formula VI is produced by combining a compound of Formula VII

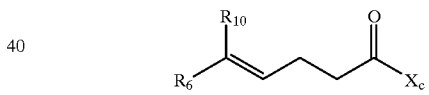

(VII)

wherein $X_c$ and m are as provided in claim 1, with a base or a mixture of a base and a Lewis acid; and
an electrophilic compound of the formula

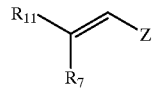

wherein $R_7$ and $R_{11}$ are as defined in claim 1 and Z is selected from the group consisting of aldehydes and alkyl halides, under reaction conditions sufficient to produce a compound of Formula VI.

6. A method according to claim 5 wherein said mixture of base and Lewis acid is a mixture of dibutylboron triflate and triethyl amine.

7. A method according to claim 5 wherein said electrophilic compound is acrolein.

8. A method according to claim 5, wherein said compound of Formula VII is [4S]-3-(1-oxo-4-pentenyl)-4-benzyl-2-oxazolidinone.

9. A method according to claim 5, wherein said compound of Formula VII is produced by reacting a chiral auxiliary with a base and a compound of the formula

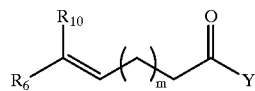

wherein m, $R_6$ and $R_{10}$ are as provided in claim 1, and Y is a strong leaving group, to produce a compound of Formula VII.

10. A method according to claim 9 wherein said chiral auxiliary is selected from the group consisting of:

(A)

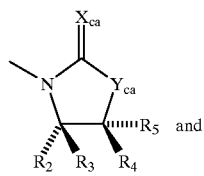

and (B)

wherein $X_{ca}$ is S or O;
$Y_{ca}$ is S or O;
$R_2$ is hydrogen, alkyl, aryl or alkylaryl;
$R_3$ is hydrogen, alkyl, aryl or alkylaryl;
$R_4$ is hydrogen, alkyl, aryl or alkylaryl; and
$R_5$ is hydrogen, alkyl, aryl or alkylaryl.

11. A method according to claim 9 wherein said strong leaving group is selected from the group consisting of halogens and carboxylates.

12. A method according to claim 9, wherein said strong leaving group is pivalate.

13. A method according to claim 9, wherein said compound of Formula VII is [4S]-3-(1-oxo-4-pentenyl)-4-benzyl-2-oxazolidinone.

14. A method according to claim 1, wherein said compound of formula V is further reacted with a reducing agent to produce a compound of the Formula X:

(X)

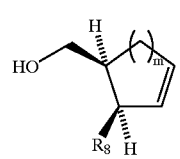

wherein m and $R_8$ is as defined in claim 1.

15. A method according to claim 14 wherein said reducing agent is selected from the group consisting of $LiBH_4$ and $LiAlH_4$.

16. A method according to claim 14, wherein said compound of Formula X is (1R,5R)-5-hydroxymethyl-2-cyclopenten-1-ol.

17. A method according to claim 1, wherein said compound of Formula V is further reacted with a base and compound of formula $R_9OH$, wherein $R_9$ is hydrogen, alkyl, aryl or alkylaryl, to produce a compound of Formula as provided in claim 10, and a compound of Formula IX:

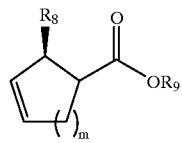

wherein m and $R_8$ are defined as in claim 1 above.

18. A method according to claim 17, wherein said compound of Formula IX is an alkylaryl ester.

* * * * *

UNITED STATES PATENT AND TRADEMARK OFFICE
CERTIFICATE OF CORRECTION

PATENT NO. : 5,973,161
DATED : October 26, 1999
INVENTOR(S) : Michael T. Crimmins Page 1 of 2

It is certified that error appears in the above-identified patent and that said Letters Patent is hereby corrected as shown below:

In the ABSTRACT please replace Formula XII with the following:

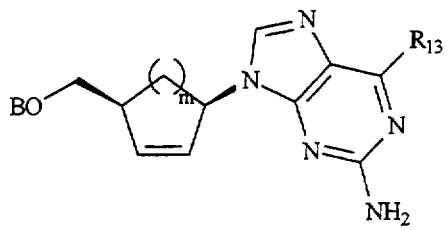

In Claim 1 and Claim 10 please replace structure (B) with the following structure:

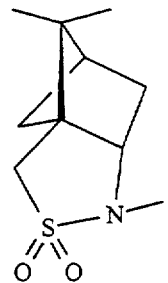

UNITED STATES PATENT AND TRADEMARK OFFICE
CERTIFICATE OF CORRECTION

PATENT NO. : 5,973,161
DATED : October 26, 1999
INVENTOR(S) : Michael T. Crimmins It is certified that error appears in the above-identified patent and that said Letters Patent is hereby corrected as shown below:

In Claim 17, column 22, line 26 please insert the term VII after the word "Formula".

In Claim 1, column 19, line 49 please replace the word "a" before the word "organic" with the word "an".

In Claim 1, column 20, line 12 please replace the word "alky" with the word "alkyl"

Signed and Sealed this

Twentieth Day of February, 2001

NICHOLAS P. GODICI

*Attest:*

*Attesting Officer*   *Acting Director of the United States Patent and Trademark Office*